(12) United States Patent
Takayama et al.

(10) Patent No.: US 10,251,628 B2
(45) Date of Patent: Apr. 9, 2019

(54) ULTRASONIC DIAGNOSTIC APPARATUS AND BIOMETRICAL EXAMINATION APPARATUS

(71) Applicant: KABUSHIKI KAISHA TOSHIBA, Minato-ku (JP)

(72) Inventors: Satoshi Takayama, Kawasaki (JP); Taeko Urano, Kawasaki (JP); Kenji Nakamura, Kawasaki (JP); Tsutomu Nakanishi, Yokohama (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 271 days.

(21) Appl. No.: 15/068,099

(22) Filed: Mar. 11, 2016

(65) Prior Publication Data

US 2016/0270662 A1 Sep. 22, 2016

(30) Foreign Application Priority Data

Mar. 17, 2015 (JP) .................................. 2015-053521

(51) Int. Cl.
*A61B 8/00* (2006.01)
*A61B 8/08* (2006.01)
(Continued)

(52) U.S. Cl.
CPC .......... *A61B 8/5207* (2013.01); *A61B 5/0037* (2013.01); *A61B 5/0075* (2013.01); *A61B 8/0825* (2013.01); *A61B 8/4416* (2013.01); *A61B 5/06* (2013.01); *A61B 8/06* (2013.01); *A61B 8/58* (2013.01)

(58) Field of Classification Search
CPC ............................ A61B 5/0059; A61B 5/7225
See application file for complete search history.

(56) References Cited

U.S. PATENT DOCUMENTS

2004/0215072 A1 10/2004 Zhu
2008/0058638 A1* 3/2008 Zhu ...................... A61B 5/0091
600/425
(Continued)

FOREIGN PATENT DOCUMENTS

JP 2000-237196 A 9/2000
JP 2004-73559 A 3/2004
(Continued)

*Primary Examiner* — Joseph M Santos Rodriguez
(74) *Attorney, Agent, or Firm* — Oblon, McClelland, Maier & Neustadt, L.L.P.

(57) ABSTRACT

According to one embodiment, an ultrasonic diagnostic apparatus comprises an ultrasonic probe, image generation circuitry, image generation circuitry, at least one light emission circuitry a plurality of optical detection circuits, a slide mechanism and analysis circuitry. The slide mechanism makes at least either the at least one light emission circuitry or the plurality of optical detection circuits slide to change positional relationships between the ultrasonic transmission/reception surface, the at least one light emission circuitry, and the plurality of optical detection circuits. The analysis circuitry analyzes a change in the light intensity detected for each of different positional relationships between the ultrasonic transmission/reception surface, the at least one light emission circuitry, and the plurality of optical detection circuits.

10 Claims, 15 Drawing Sheets

(51) Int. Cl.
*A61B 5/00* (2006.01)
*A61B 8/06* (2006.01)
*A61B 5/06* (2006.01)

(56) References Cited

U.S. PATENT DOCUMENTS

| | | |
|---|---|---|
| 2010/0094134 A1 | 4/2010 | Zhu et al. |
| 2015/0305712 A1 | 10/2015 | Urano et al. |
| 2016/0270765 A1 | 9/2016 | Takayama et al. |

FOREIGN PATENT DOCUMENTS

| | | |
|---|---|---|
| JP | 2005-331292 A | 12/2005 |
| JP | 2007-20735 A | 2/2007 |
| JP | 2009-77931 A | 4/2009 |
| JP | 2009-168670 A | 7/2009 |
| JP | 2009-232876 A | 10/2009 |
| JP | 2011-143259 A | 7/2011 |
| JP | 2014-110878 A | 6/2014 |
| JP | 2014-137338 A | 7/2014 |
| JP | 2014-239815 A | 12/2014 |
| JP | 2015-123252 A | 7/2015 |
| JP | 2015-173922 A | 10/2015 |
| JP | 2016-64113 A | 4/2016 |
| JP | 2016-171910 A | 9/2016 |
| WO | WO 2006/132218 A1 | 12/2006 |
| WO | WO 2011/027548 A1 | 3/2011 |

\* cited by examiner

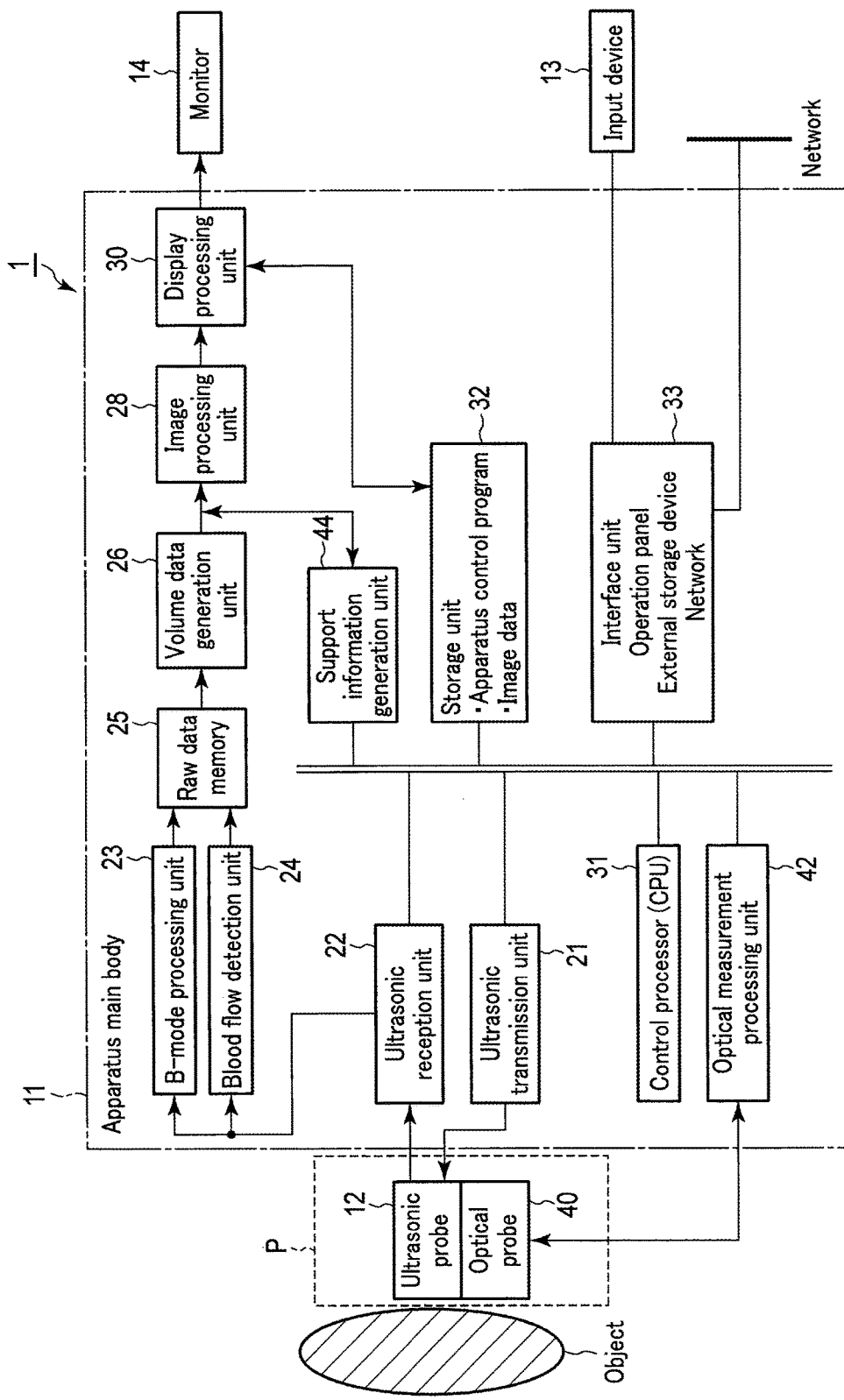
F I G. 1

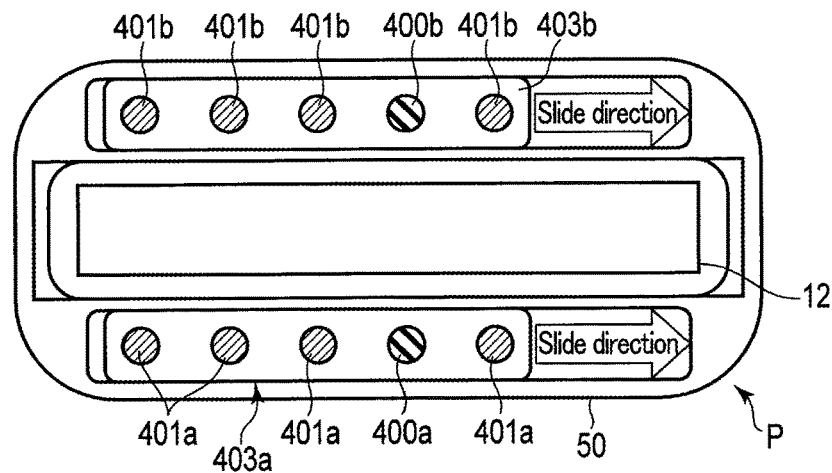
F I G. 8
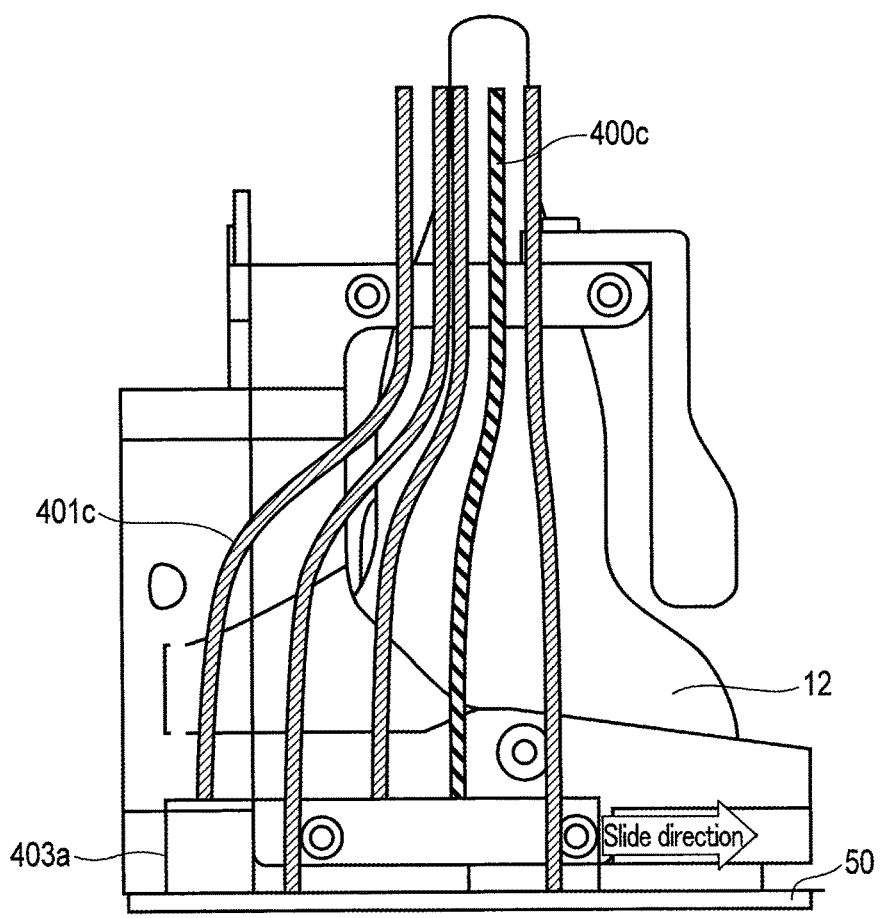
F I G. 9

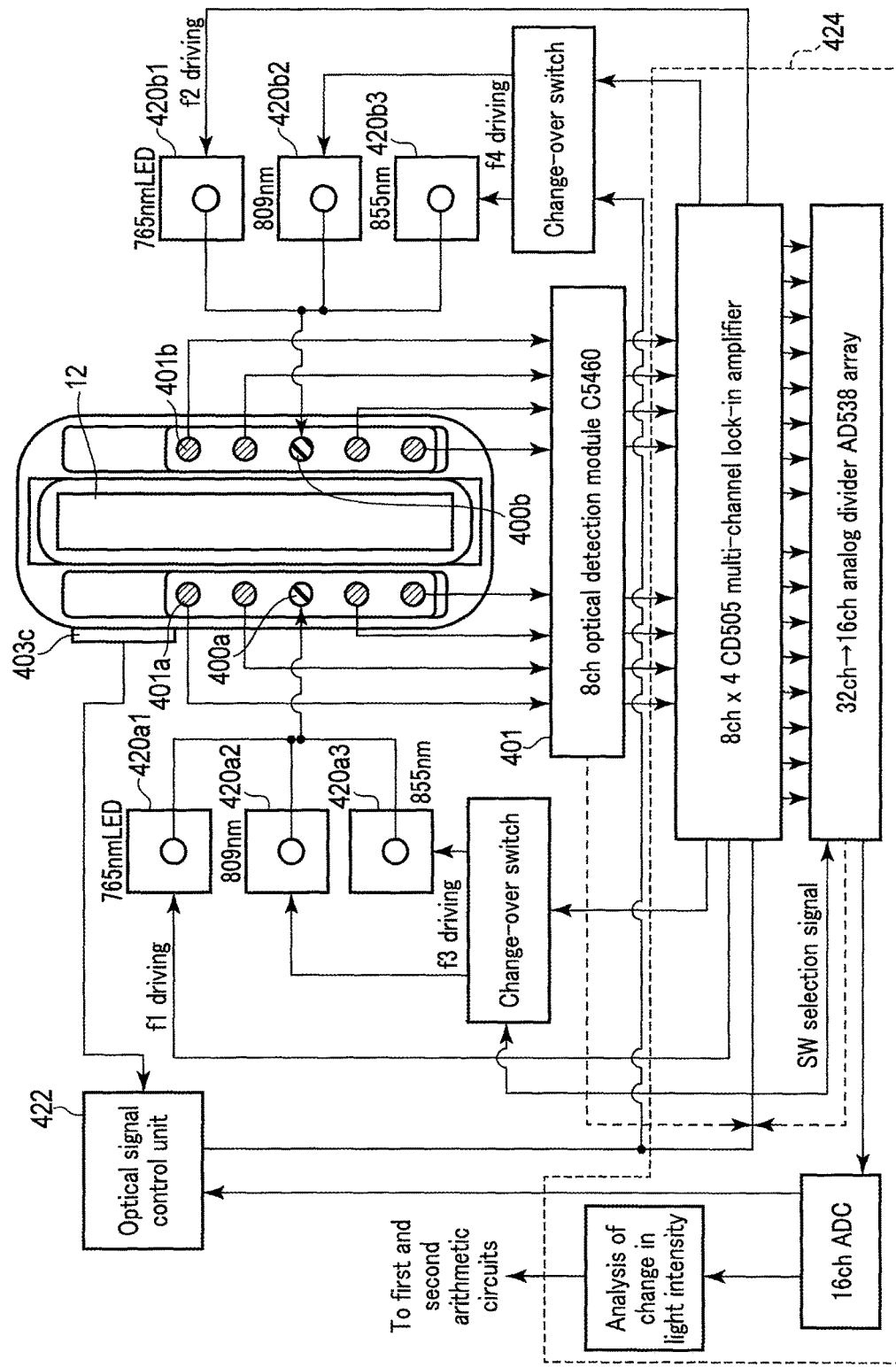
F I G. 11

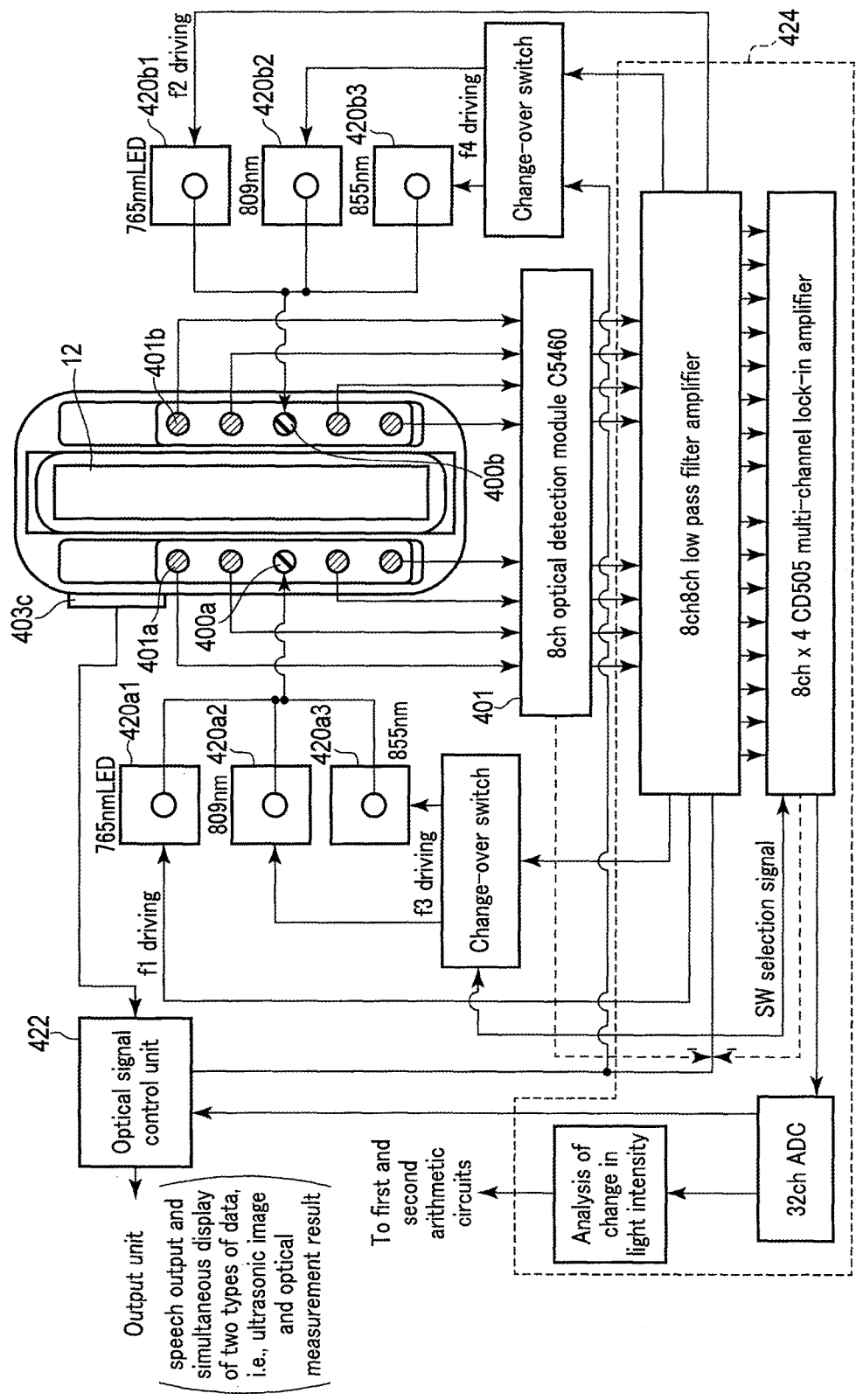
F I G. 12

Distance

Deviations in detected distance (X direction): −50 μm, 0 μm, + 50 μm
   Deviations in in-plane position (Y direction): 0 μm, + 50 μm, +100 μm
   Deviations in contact state (Z direction): 0 μm, +100 μm, +200 μm Angle Deviations in incident angle (in X-Z plane): −2°, 0°, 2°
   Deviations in detected angle (in X-Z plane): −2°, 0°, 2°

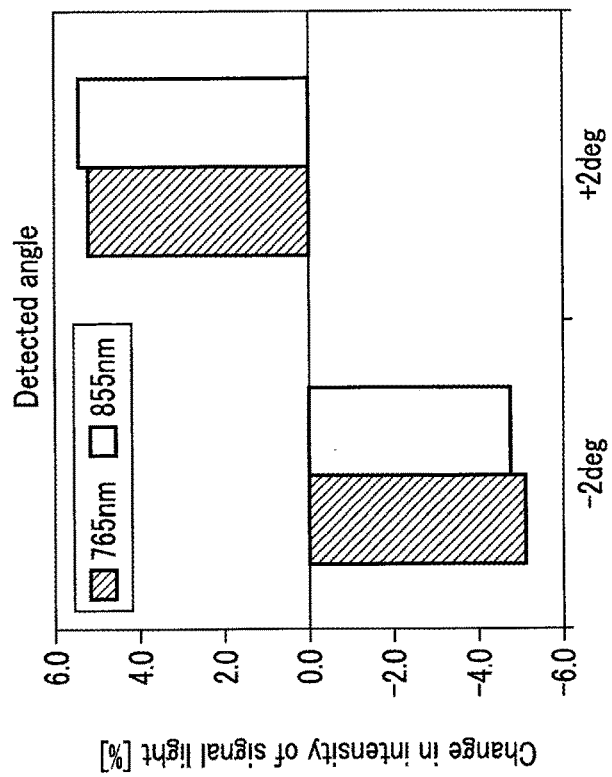
F I G. 15B
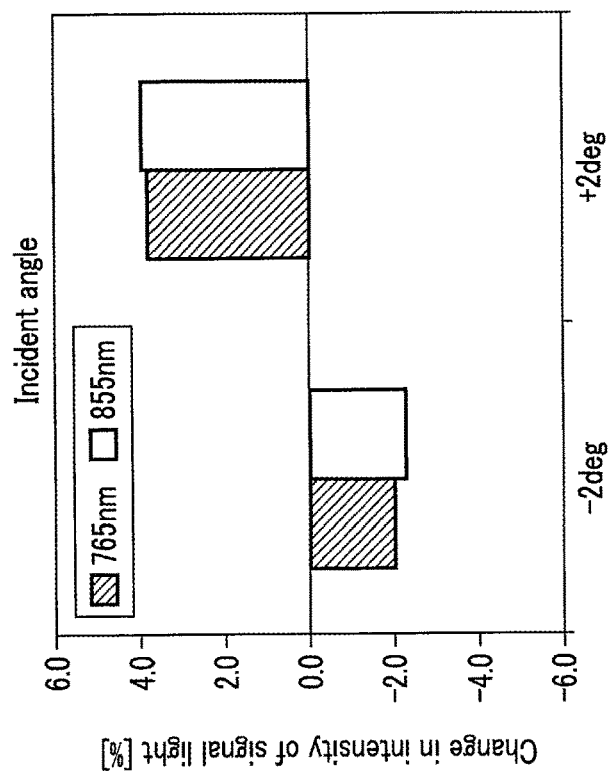
F I G. 15A

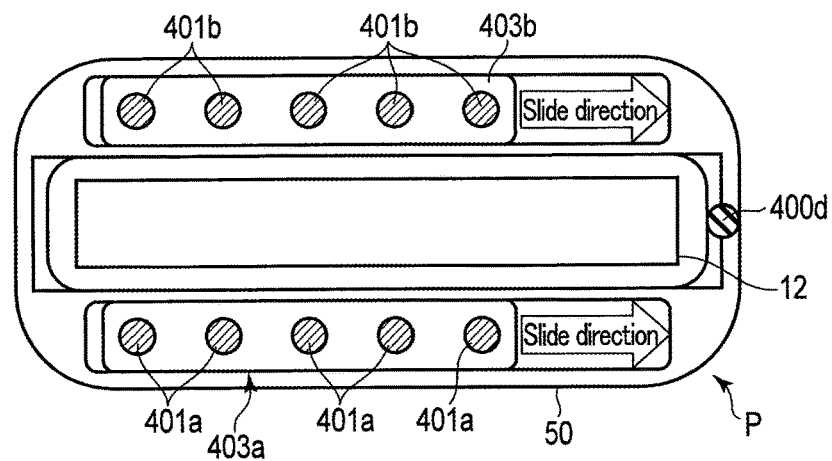
F I G. 16
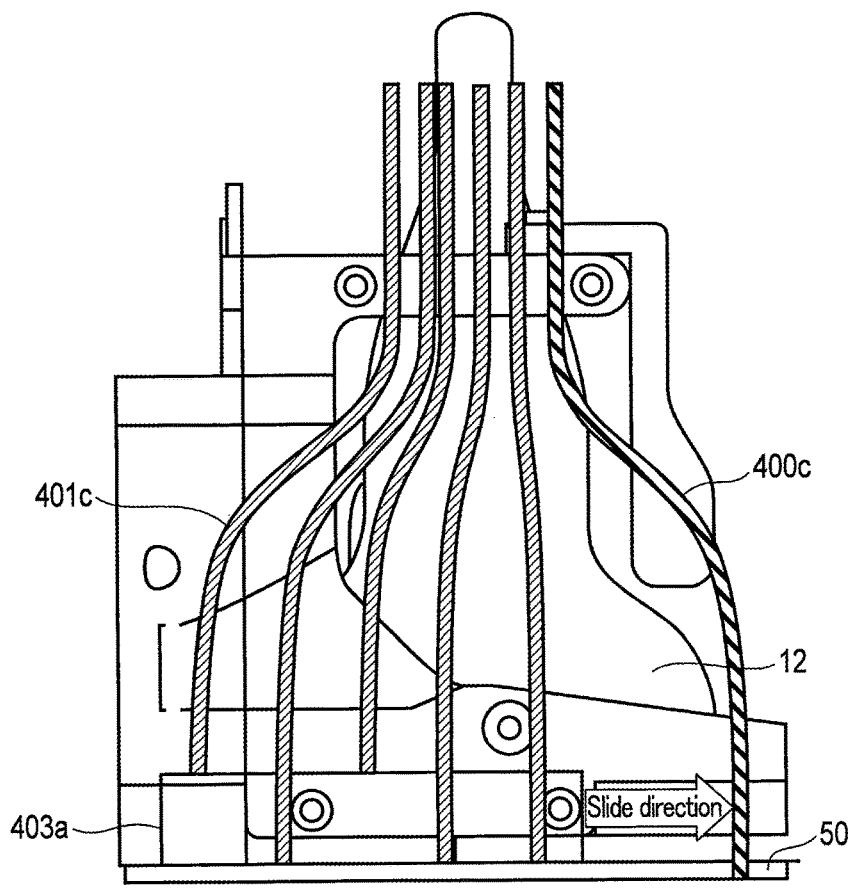
F I G. 17

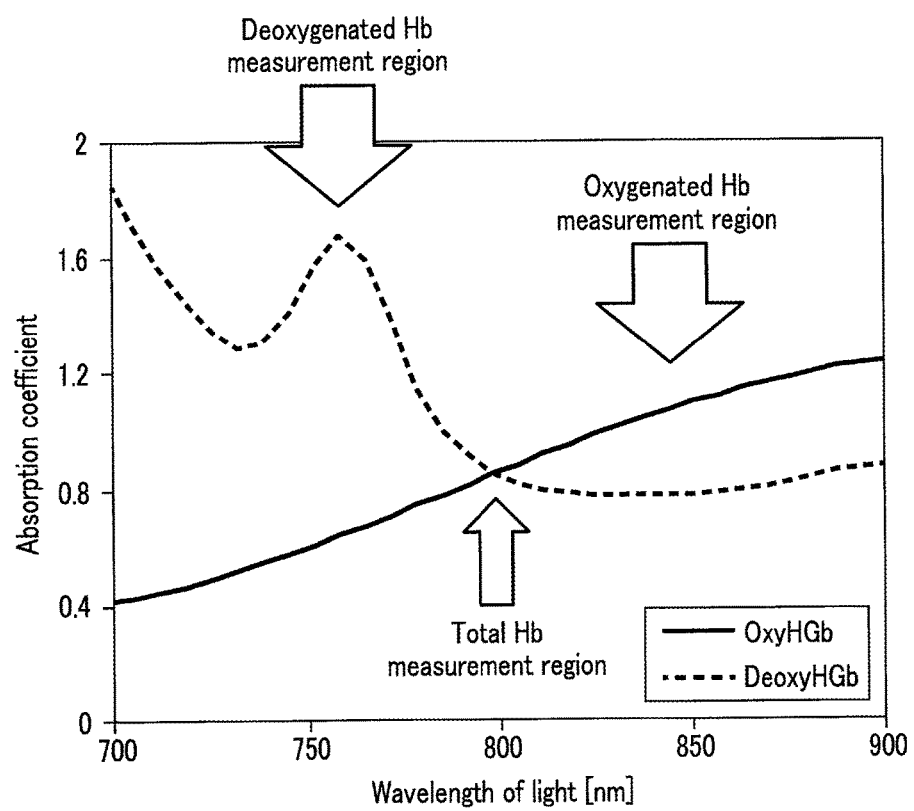
F I G. 18

ULTRASONIC DIAGNOSTIC APPARATUS AND BIOMETRICAL EXAMINATION APPARATUS

CROSS-REFERENCE TO RELATED APPLICATIONS

This application is based upon and claims the benefit of priority from the prior Japanese Patent Application No. 2015-053521, filed Mar. 17, 2015 the entire contents which are incorporated herein by reference.

FIELD

Embodiments described herein relate generally to an ultrasonic diagnostic apparatus and a biometrical examination apparatus.

BACKGROUND

There are various techniques of noninvasively measuring the inside of the living body. Optical measurement, as one of such techniques, has merits of being free from the problem of exposure to radiation and capable of selecting a compound as a measurement target by selecting a wavelength. A general biometrical measurement apparatus is designed to emit the inside of the living body with light while a light emission unit is pressed against the surface of the skin of the living body and to measure transmitted or reflected light which is transmitted through the skin again and emerges out of the living body and calculate various types of biometrical information based on the measurements. The presence of an abnormal tissue in the living body is determined by optical measurement based on the difference in light absorption coefficient between the abnormal tissue and a normal tissue. That is, the difference in absorption coefficient between normal and abnormal tissues in the living body leads to a difference in the amount of light detected based on a difference in the amount of light absorbed. Therefore, solving an inverse problem from the amount of light detected can obtain the absorption coefficient of an abnormal tissue. A characteristic of the abnormal tissue can be discriminated from the obtained absorption coefficient. In addition, the measurement position and depth are analyzed from the measured light. Such analysis techniques include a technique (spatial decomposition method) of adjusting the distance between a light emission unit (or light source) and a detector, a technique (time decomposition method) of obtaining depth information from a difference in the arrival time of light by using a light source whose intensity changes with time, and a method as a combination of them. These analysis methods implement a biometrical measurement apparatus which can acquire high-quality signals. However, the technique of imaging information based on light in the living body has the problem of a low spatial resolution. In addition, in order to obtain correct position information from the result of detecting reflected light, it is necessary to compute many data using a complicated algorithm. This makes it impossible to perform real-time determination.

Highly feasible applications of optical biometrical measurement include breast cancer examination. As described above, however, since performing optical measurement alone leads to problems in terms of resolution and analysis time, it is preferable to improve examination performance by using this technique in combination of another modality. For this reason, the present inventors have proposed a scheme of compensating for the low spatial resolution of light by using the morphological information of ultrasonic echoes. Although this scheme is expected to be capable of discriminating morphological characteristics in living body tissues and the partial distribution of morphological characteristic portions within a shorter time than in a related art, there is still room for improvement in immediate determination.

Breast cancer is one of the causes of women death. Breast cancer screening and early diagnosis have very high values in terms of reducing mortality rate and suppressing the cost of health care.

Existing methods include palpation of breast tissues and X-ray imaging for searching for suspected tissue deformation. If there is a suspected portion in an X-ray photograph, ultrasonic imaging is performed, and surgical tissue examination is further performed. A series of these examinations require much time to reach a final conclusion. In addition, since premenopausal young women have many mammary glands, high sensitivity is difficult to obtain in X-ray imaging. Therefore, screening using ultrasonic imaging has great significance for the young generation, in particular.

In general, in ultrasonic imaging, a certified operator acquires ultrasonic still images, and an expert interpreter (a plurality of interpreters in some cases) makes determination from morphological information on the images. When performing medical examination, the maximum number of persons subjected to screening per operator per day is 50 in consideration of the risk of oversights caused by the fatigue and lack of concentration of the operator.

In order to acquire a still image capturing a morphological characteristic in ultrasonic imaging, it is very important for the operator to have knowledge and experience. High skill is also required to perform accurate and quick screening. For example, standard examination times per object are 5 to 10 min. However, it sometimes takes more time for screening depending on the skill of an operator. That is, in screening based on current ultrasonic imaging, the accuracy of image acquisition may vary depending on the levels of skill of operators. When acquiring images, the operator needs to keep paying close attention to images. Besides, he/she takes charge of making determination by himself/herself, and hence a heavy metal strain is imposed on him/her even if he/she is a skilled operator. Although there is available a scheme of acquiring all image information from a moving image, there is no established technique for mechanical search using image recognition. For this reason, an interpreter searches a moving image for still images. In this case, a heavy burden is imposed on the interpreter.

In order to solve the above problem, the present applicant has proposed an apparatus with the concept of complement of ultrasonic echo diagnosis by using a compact optical examination system designed to reduce a burden on a technician by guiding the measurement position of an ultrasonic echo probe in a plane direction based on the metabolic information of the living body which is obtained by optical measurement. FIG. 18 shows the light absorption spectra of oxygenated hemoglobin and deoxygenated hemoglobin. In general, deoxygenated hemoglobin in a malignant tumor region is higher in ratio than in a healthy region, and hence an analysis result on the absorption of deoxygenated hemoglobin is one of the bases for determining the degree malignancy of a target region in optical biometrical examination. The wavelength regions of light suitable for the light absorption measurement of deoxygenated hemoglobin are 740 nm to 790 nm in the near-infrared light region and 650 nm to 690 nm in the red light region. The wavelength region of light suitable for the light absorption measurement of oxygenated hemoglobin is 830 nm to 900 nm in the near-infrared light region. The wavelength region of light to identify a total hemoglobin amount is, for example, 800 nm to 820 nm in the near-infrared light region. Specific light sources include an LED and an LD. In consideration of absorption wavelength of other biological components such as water, fat, and melanin and biodistributions, an output light intensity and a half width must be properly selected for a light source.

One of the problems in conventionally proposed biometrical measurement apparatuses is that a measurement target to which an ultrasonic echo probe is guided by an optical measurement system is not always located immediately below the probe. This problem originates from the selection of an arrangement in which the longitudinal symmetrical axis of the ultrasonic echo piezoelectric probe is orthogonal to a symmetrical axis of the optical measurement system.

In order to solve this problem, the present inventors have proposed the arrangement of a probe configured such that a symmetrical axis of an optical measurement system substantially coincides with the longitudinal axis of an ultrasonic echo piezoelectric probe (a symmetrical axis of an optical measurement system is arranged to be parallel to the longitudinal direction of the piezoelectric probe and fall within its short side). In such a typical probe arrangement, a light introducing unit is arranged at a position near a short side of the piezoelectric probe, and a plurality of detection units are symmetrically arranged near a probe short side. This avoids the problem that a measurement target is positioned outside the piezoelectric probe.

In this arrangement, however, since a measurement target is positioned at an end of an echo image, it is not possible to meet the need to guide a target to the central position to perform examination while rotating the probe. In order to solve this problem, the present inventors have selected an arrangement in which a plurality of light sources are arranged near the central position of the piezoelectric probe so as to be symmetrical with respect to an axis in the long-side direction, and a plurality of detection units to be paired with the light sources are arranged symmetrically with respect to the axis in the short-side direction of the piezoelectric probe. This arrangement makes it possible to guide a measurement target to the central position of an echo probe. In addition, the present inventors have also proposed an optical detection system which has been improved in terms of the implementation of a multiple light source scheme in order to solve the problem that the amount of light absorbed changes because the probe is brought into pressure contact with the skin.

This probe arrangement is suited to guide an abnormal region to a position immediately below the middle of the probe, but can only roughly estimate the depth and size of a region. For this reason, when, for example, it is necessary to perform image examination with a spatial resolution of 5 mm, data obtained by one measurement is not enough for the examination. Obviously, the problem can be solved by greatly increasing the numbers of light incident positions and detection positions. This requires an enormous calculation amount and an enormous calculation time. In addition, as the number of channels increases accordingly, the detection system increases in size. This makes it impossible to meet the need for a compact system which complements ultrasonic echoes.

To solve this problem, imaging can be implemented by acquiring the necessary number of data by performing a plurality of measurements with an arrangement whose relative position is properly changed. However, it is highly difficult to perform accurate positioning in biometrical examination. In addition, when the surface of the living body is scanned with a probe, the distribution of blood changes by the pressure on the skin. For this reason, bringing the probe into contact with the skin with a high repeatability also increases the difficulty in measurement. As described above, examination technicians are required to have high skills and techniques.

In order to solve the above problems, this embodiment has as its object to provide an ultrasonic diagnostic apparatus and a biometrical examination apparatus which can increase the amount of measurement data while easily and accurately measuring the relative position of an ultrasonic probe at the time of biometrical measurement when guiding the position of the probe.

BRIEF DESCRIPTION OF THE DRAWING

FIG. 1 is a block diagram showing the arrangement of an ultrasonic diagnostic apparatus 1 according to an embodiment;

FIG. 8 is a view for explaining the first modification of the probe P according to this embodiment;

FIG. 9 is a view for explaining the first modification of the probe P according to this embodiment;

FIG. 11 is a view showing the second modification of the optical measurement system of the biometrical measurement apparatus 4;

FIG. 12 is a view showing the third modification of the optical measurement system of the biometrical measurement apparatus 4;

FIGS. 15A and 15B are views showing an example of the position accuracy of the probe and a light intensity error measuring method;

FIG. 16 is a view showing an example of the probe P including the slide mechanism 403a which makes only the optical detection units 401 slide while the light emission units 400 are fixed;

FIG. 17 is a view showing an example of the probe P including the slide mechanism 403a which makes only the optical detection units 401 slide while the light emission units 400 are fixed; and FIG. 18 is a graph showing the light absorption spectra of oxygenated hemoglobin and deoxygenated hemoglobin.

DETAILED DESCRIPTION

Figure 2:
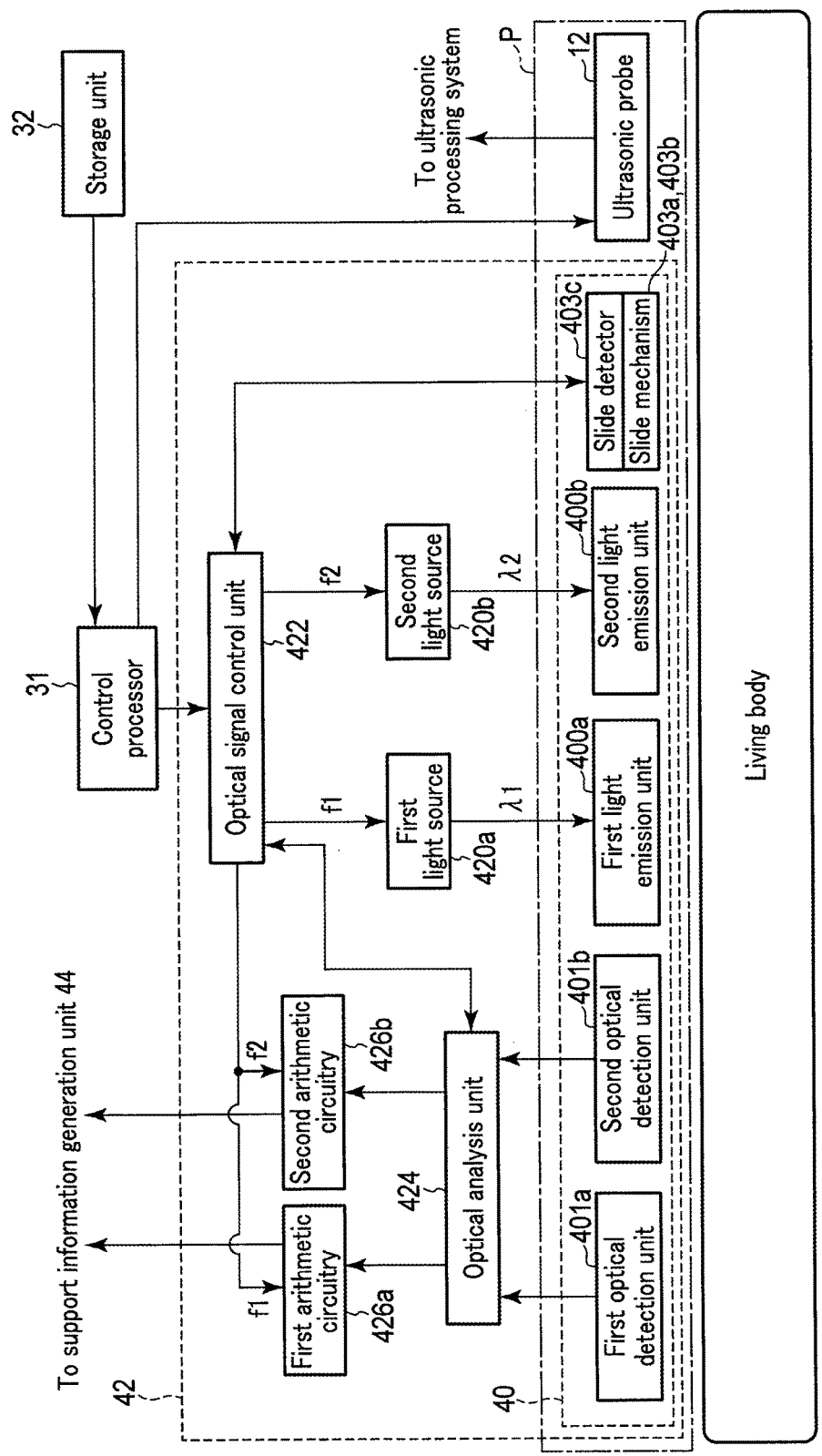
FIG. 2 is a block diagram showing the arrangement of a biometrical measurement apparatus 4 including an optical probe 40 and an optical measurement processing unit 42.

According to one embodiment, an ultrasonic diagnostic apparatus comprises an ultrasonic probe, an image generation circuitry, an image generation circuitry, at least one light emission circuitry a plurality of optical detection circuits, a slide mechanism and analysis circuitry. The ultrasonic probe transmits an ultrasonic wave from an ultrasonic transmission/reception surface to an object and receives an ultrasonic wave reflected by an inside of the object via the ultrasonic transmission/reception surface. The image generation circuitry generates an ultrasonic image by using the ultrasonic wave received by the ultrasonic probe. The at least one light emission circuitry applies light in an absorption wavelength band of a biological component from a surrounding of the ultrasonic transmission/reception surface onto the inside of the object. The plurality of optical detection circuits is arranged around the at least one light emission circuitry and to detect an intensity of light having a specific wavelength which is applied from the at least one light emission circuitry and diffused/reflected by the inside of the object. The slide mechanism makes at least either the at least one light emission circuitry or the plurality of optical detection circuits slide to change positional relationships between the ultrasonic transmission/reception surface, the at least one light emission circuitry, and the plurality of optical detection circuits. The analysis circuitry analyzes a change in the light intensity detected for each of different positional relationships between the ultrasonic transmission/reception surface, the at least one light emission circuitry, and the plurality of optical detection circuits.

An embodiment will be described below with reference to the accompanying drawing. Note that the same reference numerals in the following description denote constituent elements having almost the same functions and arrangements, and a repetitive description will be made only when required.

FIG. 1 is a block diagram showing the arrangement of an ultrasonic diagnostic apparatus 1 according to this embodiment. The ultrasonic diagnostic apparatus 1 shown in FIG. 1 includes an ultrasonic probe 12, an input device 13, a monitor 14, an ultrasonic transmission unit 21, an ultrasonic reception unit 22, a B-mode processing unit 23, a blood flow detection unit 24, a raw data memory 25, a volume data generation unit 26, an image processing unit 28, a display processing unit 30, a control processor (CPU) 31, a storage unit 32, and an interface unit 33. The ultrasonic diagnostic apparatus 1 according to the embodiment further includes an optical probe 40 and an optical measurement processing unit 42, which serve to implement a biometrical measurement apparatus 4, and a scanning support information creation unit 44 which generates scanning support information for supporting the placement operation of the ultrasonic probe 12.

Note that this embodiment will exemplify the ultrasonic diagnostic apparatus 1 incorporating the biometrical measurement apparatus (integrated with the biometrical measurement apparatus). However, this is not exhaustive, and the biometrical measurement apparatus and the ultrasonic diagnostic apparatus may be separate structures.

The ultrasonic probe 12 is a device (probe) which transmits ultrasonic waves to an object, typically the living body, and receives reflected waves from the object based on the transmitted ultrasonic waves. The ultrasonic probe 12 has, on its distal end, an array of a plurality of piezoelectric transducers, a matching layer, a backing member, and the like. The piezoelectric transducers transmit ultrasonic waves in a desired direction in a scan region based on driving signals from the ultrasonic transmission unit 21, and convert reflected waves from the object into electrical signals. The matching layer is an intermediate layer which is provided for the piezoelectric transducers to make ultrasonic energy efficiently propagate. The backing member prevents ultrasonic waves from propagating backward from the piezoelectric transducers. When the ultrasonic probe 12 transmits an ultrasonic wave to the object, the transmitted ultrasonic wave is sequentially reflected by a discontinuity surface of acoustic impedance of internal body tissue, and is received as an echo signal by the ultrasonic probe 12. The amplitude of this echo signal depends on an acoustic impedance difference on the discontinuity surface by which the echo signal is reflected. The echo produced when a transmitted ultrasonic pulse is reflected by a moving blood flow is subjected to a frequency shift depending on the velocity component of the moving body in the ultrasonic transmission/reception direction by the Doppler effect.

Note that in this embodiment, the ultrasonic probe 12 is a one-dimensional array probe having a plurality of ultrasonic transducers arrayed along a predetermined direction. However, this is not exhaustive, and the ultrasonic probe 12 may be a two-dimensional array probe (i.e., a probe having ultrasonic transducers arranged in the form of a two-dimensional matrix) or a mechanical 4D probe (i.e., a probe which can execute ultrasonic scanning while mechanically swinging an ultrasonic transducer array), which can acquire volume data.

The input device 13 is connected to an apparatus body 11 and includes various types of switches which are used to input, to the apparatus body 11, various types of instructions, conditions, an instruction to set a region of interest (ROI), various types of image quality condition setting instructions, and the like from an operator, a switch for switching between a rough search mode and a fine adjustment mode which will be described later, buttons, a trackball, a mouse, and a keyboard. In addition, the input device 13 includes a button or the like for instructing the timing to capture paracentesis information including the position of the tip of a puncture needle in a paracentesis support function.

The monitor 14 displays morphological information and blood flow information in the living body as images based on video signals from the display processing unit 30.

The ultrasonic transmission unit 21 is circuitry which includes trigger generation circuitry, delay circuitry, and pulser circuitry (none of which are shown). The trigger generation circuitry repetitively generates trigger pulses for the formation of transmission ultrasonic waves at a predetermined rate frequency fr Hz (period: 1/fr sec). The delay circuitry gives each trigger pulse a delay time necessary to focus an ultrasonic wave into a beam and determine transmission directivity for each channel. The pulse circuitry applies a driving pulse to the probe 12 at the timing based on this trigger pulse.

The ultrasonic reception unit 22 is a circuitry which includes an amplifier circuitry, an A/D converter, a delay circuitry, and adder (none of which are shown). The amplifier circuitry amplifies an echo signal received via the probe 12 for each channel. The A/D converter converts each analog echo signal into a digital echo signal. The delay circuitry gives the digitally converted echo signals delay times necessary to determine reception directivities and perform reception dynamic focusing. The adder then performs addition processing for the signals. With this addition, a reflection component from a direction corresponding to the reception directivity of the echo signal is enhanced to form a composite beam for ultrasonic transmission/reception in accordance with reception directivity and transmission directivity.

The B-mode processing unit 23 is circuitry which receives an echo signal from the reception unit 22, and performs logarithmic amplification, envelope detection processing, and the like for the signal to generate data whose signal intensity is expressed by a luminance level.

The blood flow detection unit 24 is circuitry which extracts a blood flow signal from the echo signal received from the ultrasonic reception unit 22, and generates blood flow data. In general, the blood flow detection unit 24 extracts a blood flow by CFM (Color Flow Mapping). In this case, the blood flow detection unit 24 analyzes the blood flow signal to obtain blood flow information such as mean velocities, variances, and powers as blood flow data at multiple points.

The raw data memory 25 generates B-mode raw data as B-mode data on three-dimensional ultrasonic scanning lines by using a plurality of B-mode data received from the B-mode processing unit 23. The raw data memory 25 generates blood flow raw data as blood flow data on three-dimensional ultrasonic scanning lines by using a plurality of blood flow data received from the blood flow detection unit 24. Note that for the purpose of reducing noise or smooth concatenation of images, a three-dimensional filter may be inserted after the raw data memory 25 to perform spatial smoothing.

The volume data generation unit 26 is processing circuitry which generates B-mode volume data or blood flow volume data by executing raw/voxel conversion including interpolation processing in consideration of spatial positional information.

The image processing unit 28 is processing circuitry which performs predetermined image processing such as volume rendering, MPR (Multi Planar Reconstruction), and MIP (Maximum Intensity Projection) for the volume data received from the volume data generation unit 26.

Note that for the purpose of reducing noise or smooth concatenation of images, a two-dimensional filter may be inserted after the image processing unit 28 to perform spatial smoothing.

The display processing unit 30 is processing circuity which executes various types of processing associated with a dynamic range, luminance (brightness), contrast, γ curve correction, RGB conversion, and the like for various types of image data generated/processed by the image processing unit 28.

The control processor (CPU) 31 has the function of an information processing apparatus (computer) and controls the operation of each constituent element. The control processor 31 also executes processing in accordance with an ultrasonic probe operation support function (to be described later).

The storage unit 32 includes, for example, a semiconductor storage device such as a Flash SSD (Solid State Disk) serving as a semiconductor storage element, and an HDD (Hard Disk Drive). The storage unit 32 stores a dedicated program for implementing the ultrasonic probe operation support function (to be described later), obtained volume data, diagnosis information (patient ID, findings by doctors, and the like), a diagnostic protocol, transmission/reception conditions, and other data groups. The storage unit 32 is also used to store images in the image memory (not shown), as needed. It is possible to transfer data in the storage unit 32 to an external peripheral device via the interface unit 33.

The interface unit 33 is an interface circuit associated with the input device 13, a network, and a new external storage device (not shown). In addition, an external biometrical measurement apparatus can be connected to this ultrasonic diagnostic apparatus main body 11 via the interface unit 33. The interface unit 33 can transfer data such as ultrasonic images obtained by this apparatus, analysis results, and the like to other apparatuses via a network.

The scanning support information creation unit 44 is circuitry which calculates at least one the degree of adhesion between the ultrasonic probe 12 and the surface of an object and the three-dimensional azimuth and distance (proximity) of an abnormal region in an object based on the three-dimensional position and distance of the abnormal region which are acquired at each measurement position upon movement by a slide mechanism 403a. The scanning support information creation unit 44 then supports the operation of the ultrasonic probe by generating and outputting scanning support information for more favorably inducing the position, orientation, posture, pressure, and the like of the ultrasonic probe 12 with respect to the object and the diagnostic target region based on the calculation result, thereby supporting the operation of the ultrasonic probe. Note that as specific processing performed by the scanning support information creation unit 44, for example, the technique disclosed in Jpn. Pat. Appln. KOKAI Publication No. 2014-110878 can be adopted. The monitor 14 displays the generated scanning support information in a form.

Figure 3:
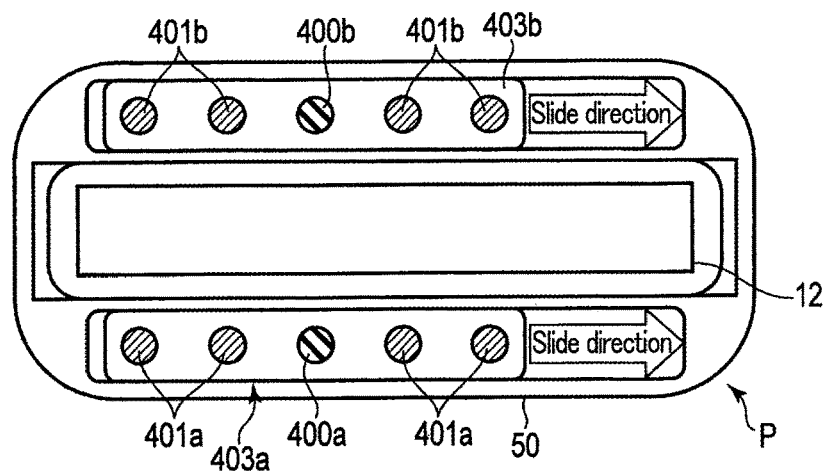
FIG. 3 is a view when a probe P is seen from the object contact surface side, explaining an example of the placement of light emission units 400 and optical detection units 401 with respect to the ultrasonic transmission/reception surface of an ultrasonic probe 12 and a slide mechanism for making the light emission units 400 and the optical detection units 401 slide together.
Figure 4:
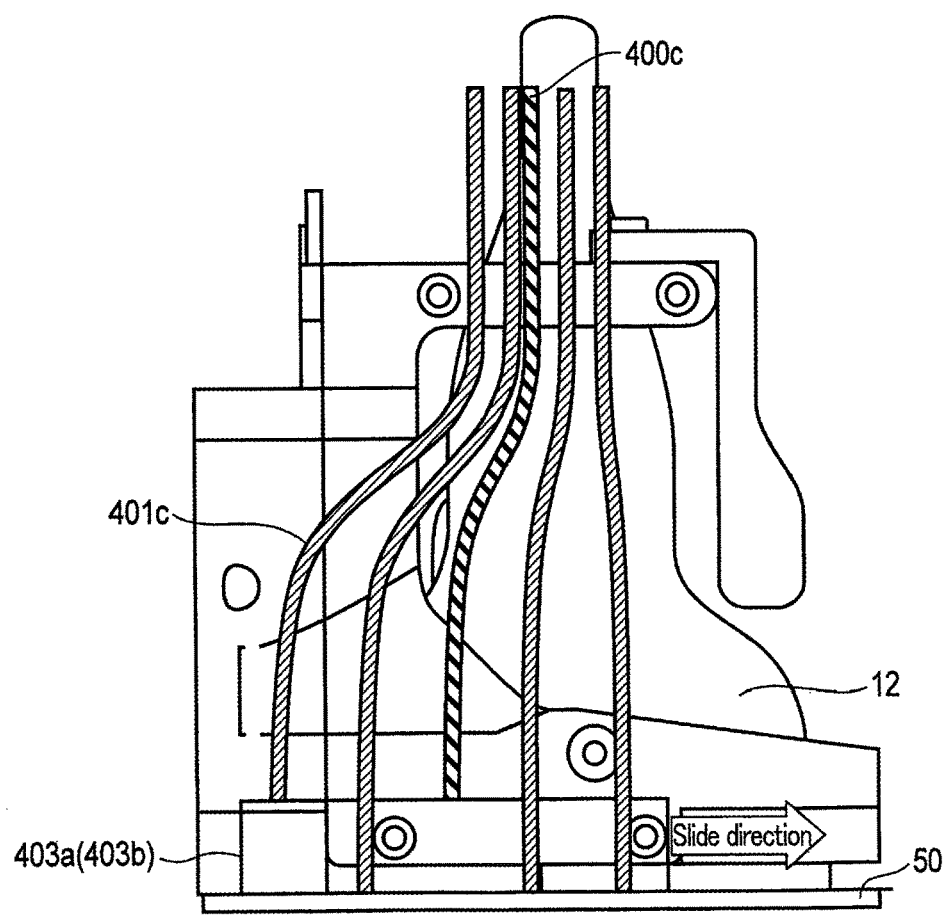
FIG. 4 is a side view of the probe P including the ultrasonic probe 12 and the optical probe 40.

FIG. 2 is a block diagram of the biometrical measurement apparatus 4 including the optical probe 40 and the optical measurement processing unit 42. FIG. 3 is a view when the probe P is seen from the object contact surface side, explaining an example of the placement of light emission units 400 and optical detection units 401 with respect to the ultrasonic transmission/reception surface of the ultrasonic probe 12 and a slide mechanism for moving the light emission units 400 and the optical detection units 401 together along the longitudinal direction of the ultrasonic transmission/reception surface of the ultrasonic probe 12. FIG. 4 is a side view of the probe P including the ultrasonic probe 12 and the optical probe 40.

As shown in FIGS. 2 and 3, the optical probe 40 includes at least two light emission units 400 (a first light emission unit 400a and a second light emission unit 400b arranged on the two sides of the middle of the ultrasonic transmission/reception surface of the ultrasonic probe 12 in the case shown in FIG. 3), and the plurality of optical detection units 401, the slide mechanism 403a, and a slide detector 403c which are arranged so as to sandwich the first light emission unit 400a xand the second light emission unit 400b on the two sides of the middle of the ultrasonic transmission/reception surface of the ultrasonic probe 12. The plurality of light emission units 400 and the plurality of optical detection units 401 are line-symmetrically arranged with respect to the central axis of the ultrasonic transmission/reception surface of the ultrasonic probe 12 in the longitudinal direction and arranged at equal intervals along the longitudinal direction of the ultrasonic transmission/reception surface. This is merely an example; there is a modification in which the positional intervals between the above units are adjusted in consideration of the distances to the optical detection units 401 which they face.

The first light emission unit 400a and the second light emission unit 400b respectively emit an object with light (near-infrared light) generated by a first light source 420a and a second light source 420b. Different driving frequencies f1 and f2 are respectively supplied to the first light emission unit 400a and the second light emission unit 400b. As a result, the first light emission unit 400a and the second light emission unit 400b respectively emit the object with light beams having specific wavelengths at the different driving frequencies.

The first light source 420a and the second light source 420b are light-emitting elements such as semiconductor lasers, light-emitting diodes, solid-state lasers, or gas lasers which generate light having a wavelength exhibiting low biological absorption (e.g., light in the wavelength range of 600 nm to 1,800 nm, which is near the wavelength band called the biological window) and light having a specific wavelength exhibiting an increase in the amount of absorption of light in an abnormal region (e.g., light in the wavelength range of 750 nm to 850 nm, which falls within the wavelength band called the biological window and at which hemoglobin in blood absorbs light). Light beams generated by the first light source 420a and the second light source 420b are respectively supplied to the first light emission unit 400a and the second light emission unit 400b via, for example, an optical fiber 400c shown in FIG. 4. The flexible optical fiber 400c reduces the influence of the deformation of the optical system caused by sliding. Different driving frequencies are supplied to the first light emission unit 400a and the second light emission unit 400b. As a result, the first light emission unit 400a and the second light emission unit 400b emit the object with light beams having specific wavelengths at the different driving frequencies. Assume that in this embodiment, the first light source 420a and the second light source 420b generate light beams having the same wavelength. However, this is not exhaustive, and the first light source 420a and the second light source 420b may generate light beams having different wavelengths, as described later.

The plurality of optical detection units 401 are formed from a plurality of detection elements which have detection surfaces formed from, for example, end portions of optical fibers 401c shown in FIG. 4, and photoelectrically convert reflected light beams from the inside of the object which are input from the detection surfaces via optical waveguide portions. The flexible optical fibers 401c reduce the influence of the deformation of the optical system caused by sliding. As each detection element, for example, a CCD, APD, photomultiplier tube, or the like can be adopted, as well as a light-receiving element such as a photodiode or phototransistor. The contact surfaces of each light emission unit 400 and each optical detection unit 401 with respect to the object may be provided with optical matching layers. Although FIG. 4 shows each optical fiber 401c in an exposed state, the entire portion, of the fiber portion, which moves upon sliding, is preferably covered with a cover in consideration of the convenience of an examiner.

As shown in FIGS. 3 and 4, the slide mechanism 403a is a moving mechanism which moves the plurality of light emission units 400 and the plurality of optical detection units 401 together along the longitudinal direction of the ultrasonic transmission/reception surface of the ultrasonic probe 12. As the slide mechanism 403a moves each light emission unit 400 and each optical detection unit 401, they can acquire data concerning detected light w0ith respect to a plurality of positions of the ultrasonic transmission/reception surface of the ultrasonic probe 12 along the longitudinal direction (i.e., a plurality of emission positions and a plurality of detection positions along the longitudinal direction).

When moving the plurality of light emission units 400 and the plurality of optical detection units 401 together along the longitudinal direction of the ultrasonic transmission/reception surface of the ultrasonic probe 12, the slide detector 403c detects measurement positions at which optical measurement has been performed (i.e., the position of each optical detection unit 401 and the position of each light emission unit 400 in optical measurement) with reference to, for example, initial positions. The detected measurement positions are output to an optical signal control unit 422.

Note that it is possible to perform optical measurement accompanying a moving operation by the slide mechanism 403a and the slide detector 403c at arbitrary positions while detecting arbitrary slide positions using a potentiometer and the like and continuously moving the plurality of light emission units 400 and the plurality of optical detection units 401 along the longitudinal direction of the ultrasonic transmission/reception surface. However, it makes it easier to perform data analysis by improving the position accuracy of multiple measurements and always maintaining a constant displacement. For this reason, the slide mechanism 403a preferably includes a mechanism capable of temporarily fixing a measurement position, and the slide detector 403c preferably includes a detector which detects the temporarily fixed position.

Figure 5A:
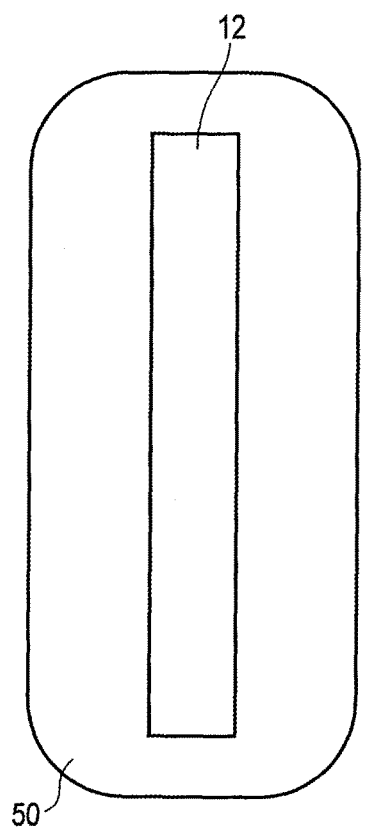
FIGS. 5A and 5B are views showing an optical measurement sole.
Figure 5B:
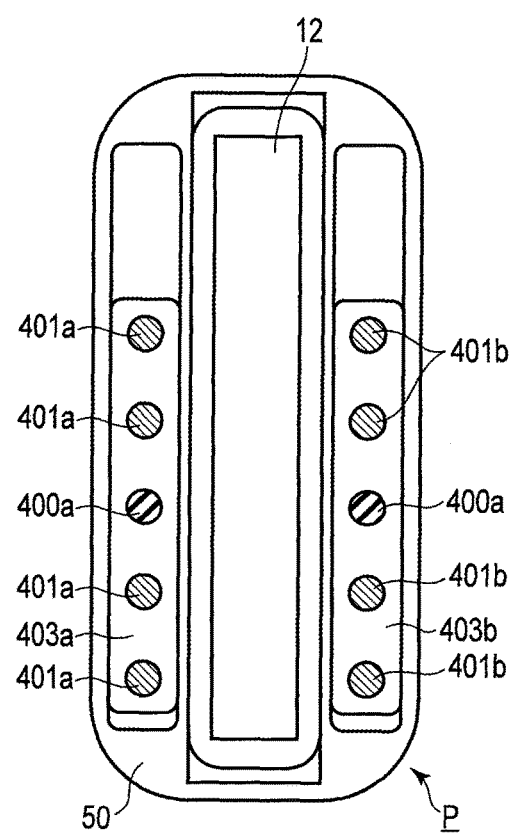

The contact surface side of the plurality of light emission units 400 and the plurality of optical detection units 401 with respect to an object is provided with an optical measurement sole like that shown in FIGS. 5A and 5B, which covers the plurality of light emission units 400 and the plurality of optical detection units 401. The optical measurement sole has a window portion for exposing the ultrasonic transmission/reception surface of the ultrasonic probe 12. The ultrasonic probe 12 is accurately fitted in the window portion. In addition, the ultrasonic transmission/reception surface of the ultrasonic probe 12 and the optical measurement sole are adjusted to the same level. Since as light used for measurement according to this embodiment, light in the near-infrared region is used, the optical measurement sole is formed from a visible light cut filter.

The optical signal control unit 422 dynamically or statically controls the biometrical measurement apparatus 4. For example, the optical signal control unit 422 controls the first light source 420a and the second light source 420b (the first light source 420a and the second light source 420b have different driving ranges in this embodiment, in particular) under the control of the control processor 31 of the ultrasonic diagnostic apparatus 1 so as to make the first light emission unit 400a and the second light emission unit 400b emit the object with light at predetermined timings, predetermined frequencies, intensities, and an intensity variation period T. In addition, the optical signal control unit 422 controls an optical analysis unit 424 so as to execute analysis processing corresponding to light with a predetermined driving period at a predetermined timing.

The optical analysis unit 424 includes a multi-channel lock-in amplifier. The optical analysis unit 424 selects periods f1 and f2, detects only predetermined signals, and amplifies them. The optical analysis unit 424 then converts the signals into digital signals. The optical analysis unit 424 also analyzes a change in the intensity of detected light between the optical detection units 401.

Based on a change in the intensity of detected light between the optical detection units 401, an arithmetic circuitry 426 calculates the three-dimensional position and distance of an abnormal region indicating a predetermined light absorption coefficient in the object (e.g., a region which absorbs light with a specific wavelength more than a normal tissue) with reference to the degrees of adhesion between the plurality of optical detection units 401 and the surface of the object, the depth of the abnormal region from the surface of the object, and a predetermined position (e.g., the light emission unit 400, the ultrasonic transmission/reception surface center of the ultrasonic probe 12, or the like). The calculation results obtained by the arithmetic circuitry 426 are sent to the scanning support information creation unit 44 for each measurement position.

Figure 6:
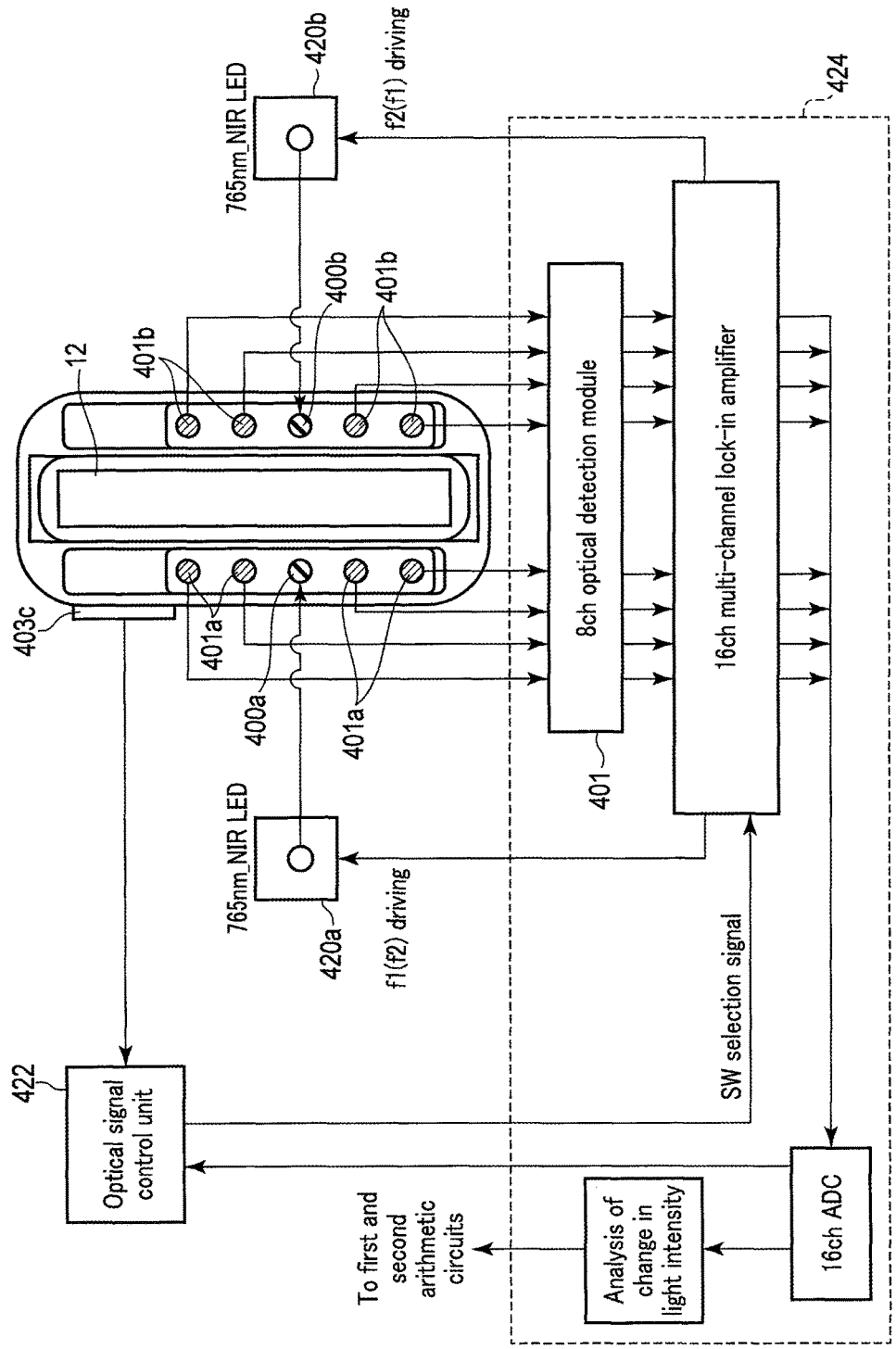
FIG. 6 is a view showing an example of the arrangement of the optical measurement system of the biometrical measurement apparatus 4.

FIG. 6 is a view showing an example of the arrangement of the optical measurement system of the biometrical measurement apparatus 4. The optical measurement system of the biometrical measurement apparatus 4 will be described in more detail with reference to FIG. 6. As the first light source 420a and the second light source 420b, for example, LEDs with wavelengths near 765 nm are used. The two LEDs are blinked at the different driving frequencies f1 and f2. As signals with the driving frequencies f1 and f2, phase detection reference signals from the multi-channel lock-in amplifier (to be described later) are used. Light beams generated by the first light source 420a and the second light source 420b are transferred from the LEDs to the first light emission unit 400a and the second light emission unit 400b via optical fibers. The first light emission unit 400a and the second light emission unit 400b emit the living body with light. Light from the living body enters each optical detection unit 401 and is transferred to an 8 ch optical detection module constituted by photoelectric conversion elements (a photodiode, avalanche photodiode, phototransistor, and the like) via an optical fiber. The 16 ch multi-channel lock-in amplifier of the optical analysis unit 424 amplifies optical signals corresponding to the driving frequencies f1 and f2. A 16 ch A/D-converter converts the optical signals, thereby analyzing changes in the intensity of light. These processes are executed for optical signals acquired at the respective measurement positions upon movement by the slide mechanism 403a.

(Optical Biometrical Measurement Accompanying Movement by Slide Mechanism)

The biometrical measurement apparatus 4 according to this embodiment executes optical biometrical measurement (i.e., a series of operations including emitting the inside of the living body with light by the plurality of light emission units 400 and detecting light from the inside of the living body by the plurality of optical detection units 401) while causing the slide mechanism 403a to move the plurality of light emission units 400 and the plurality of optical detection units 401 along the longitudinal direction of the ultrasonic transmission/reception surface. Therefore, optical signals are acquired at a plurality of measurement positions along the longitudinal direction of the ultrasonic transmission/reception surface. This can increase the amount of data used for the calculation of, for example, the depth of an abnormal region from the surface of the object by an amount corresponding to the number of measurement positions. In addition, at the time of slide measurement, since the sole portion formed from a visible light cut filter material is pressed against the surface of the skin with a constant force and the interchange of blood in an examination region at of each measurement is suppressed, it is possible to perform multiple measurements with a small measurement error.

Note that any technique can be used for optical measurement at each measurement position. This embodiment will exemplify a case in which optical measurement is performed in accordance with the rough search mode and the fine adjustment mode while the slide mechanism 403a makes the plurality of light emission units 400 and the plurality of optical detection units 401 slide, and, for example, the depth of an abnormal region from the surface of the object is calculated. In this case, the rough search mode is a mode for widely searching for an abnormal region when adjusting the position of the probe P on the surface of the living body so as to make the ultrasonic scan slice of the ultrasonic probe 12 include a diagnostic target region (a region recognized as the abnormal region or suspected to have abnormality) in the living body. The fine adjustment mode is a mode for accurately searching for the abnormal region when adjusting the position of the ultrasonic probe 12 on the surface of the living body.

Figure 7A:
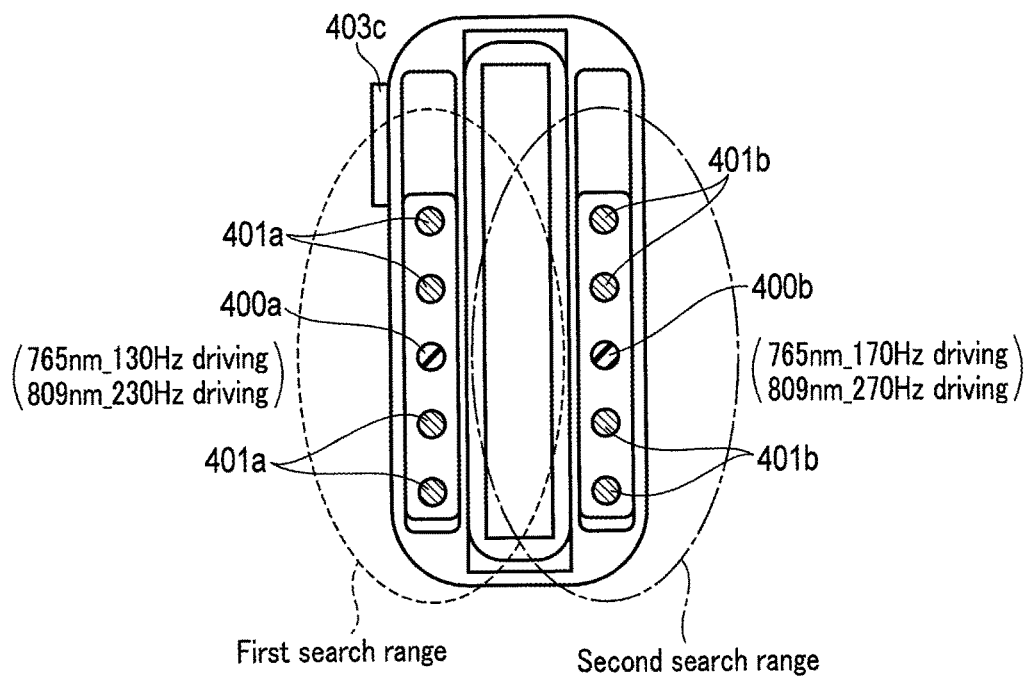
FIGS. 7A and 7B are views for explaining optical measurements respectively based on a rough search mode and a fine adjustment mode.

As shown in FIG. 7A, in the rough search mode, the first light emission unit 400a is paired with a plurality of optical detection units 401a, and the second light emission unit 400b is paired with a plurality of optical detection units 401b (that is, the light emission unit and the detection units arranged on the same side of the ultrasonic probe 12 are paired).

After the pairing, optical biometrical measurement is executed at a plurality of measurement positions, while the slide mechanism 403a performs a sliding operation, by using a region (first search range) searched by the first light emission unit 400a and the plurality of optical detection units 401a and a region (second search range) searched by the second light emission unit 400b and the plurality of optical detection units 401b. At this time, for example, if a signal in a specific frequency band corresponding to a diagnostic target region which is detected from the second search range is higher in intensity than that from the first search range, it indicates that the diagnostic region exists closer to the second search range than the center (long axis) of the ultrasonic probe 12. On the contrary, if such a signal detected from the first search range is higher in intensity than that from the second search range, it indicates that the diagnostic region exists closer to the first search range than the center (long axis) of the ultrasonic probe 12. In the rough search mode, relatively wide regions for searching for an abnormal region can be set on the two sides of the ultrasonic emission surface of the ultrasonic probe 12. It can be said from these characteristics that this mode is suitable to guide a diagnostic target region near the ultrasonic probe.

Figure 7B:
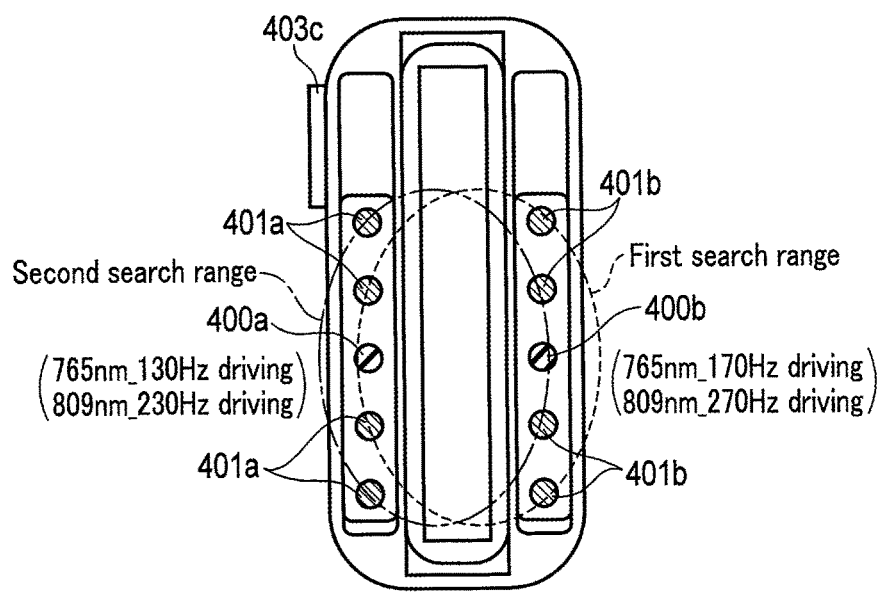

In contrast, the fine adjustment mode is executed after, for example, rough position adjustment is performed through the rough detection mode. As shown in FIG. 7B, in the fine adjustment mode, the first light emission unit 400a is paired with the plurality of optical detection units 401b, and the second light emission unit 400b is paired with the plurality of optical detection units 401a (that is, the light emission units and the detection units arranged on the two sides of the ultrasonic probe 12 are respectively paired).

After the pairing, optical biometrical measurement is executed at a plurality of measurement positions, while the slide mechanism 403a performs a sliding operation, by using a region (first search range) searched by the first light emission unit 400a and the plurality of optical detection units 401b and a region (second search range) searched by the second light emission unit 400b and the plurality of optical detection units 401a. At this time, for example, it is possible to narrow down the position of a diagnostic target region near the center of the probe P by comparing the intensity of a signal in a specific frequency band corresponding to the diagnostic target region which is detected from the first search range with that detected from the second search region. In the fine adjustment mode, a region for searching for an abnormal region is set so as to include the ultrasonic emission surface of the ultrasonic probe 12. It can be said from these characteristics that this mode is suitable to accurately guide a diagnostic target region into the ultrasonic scanning surface.

The optical analysis unit 424 analyzes a change in the intensity of detected light between the optical detection units 401 at the respective measurement positions. The arithmetic circuitry 426 calculates the depth of an abnormal region from the surface of the object which indicates a predetermined light absorption coefficient in the object, the three-dimensional position, and the distance, for each measurement position, based on the analysis result obtained by the optical analysis unit 424 (a change in the intensity of detected light between the optical detection units 401).

When guiding the position of the ultrasonic probe 12 in ultrasonic image diagnosis, an optical signal corresponding to each measurement position in each of the rough search mode and the fine adjustment mode is subjected to predetermined processing in the optical analysis unit 424, first arithmetic circuitry 426a, and second arithmetic circuitry 426b, and the resultant signal is sent as information concerning the position of the diagnostic target region to the scanning support information creation unit 44. Based on the received information concerning the diagnostic target region, the scanning support information creation unit 44 generates and outputs scanning support information for more favorably guiding the position, orientation, posture, pressure, and the like of the probe P with respect to the object and the diagnostic target region. For example, the monitor 14 displays the output scanning support information in a predetermined form.

Note that the rough search mode and the fine adjustment mode are switched from each other by, for example, an operation with the input device 13. However, this is not exhaustive. For example, the apparatus may automatically select the rough search mode or the fine adjustment mode by comparing the distance between a diagnostic target region and the ultrasonic transmission/reception surface with a predetermined threshold.

(First Modification)

FIGS. 8 and 9 are views for explaining the first modification of the probe P according to this embodiment. As compared with the case shown in FIGS. 3 and 4, in the case shown in FIGS. 8 and 9, on each of arrays along the two sides of the ultrasonic transmission/reception surface along the longitudinal direction, the plurality of optical detection units 401 are asymmetrically arranged with respect to the light emission unit 400 (that is, the three optical detection units 401 are arranged on one side of the light emission unit 400 on one array, while one optical detection unit 401 is arranged on the other side). Asymmetrically arranging the optical detection units 401 with respect to the light emission unit 400 in this manner makes it possible to set a large incidence/detection distance to facilitate detecting an abnormal region or the like at a deep position in an object.

Figure 10:
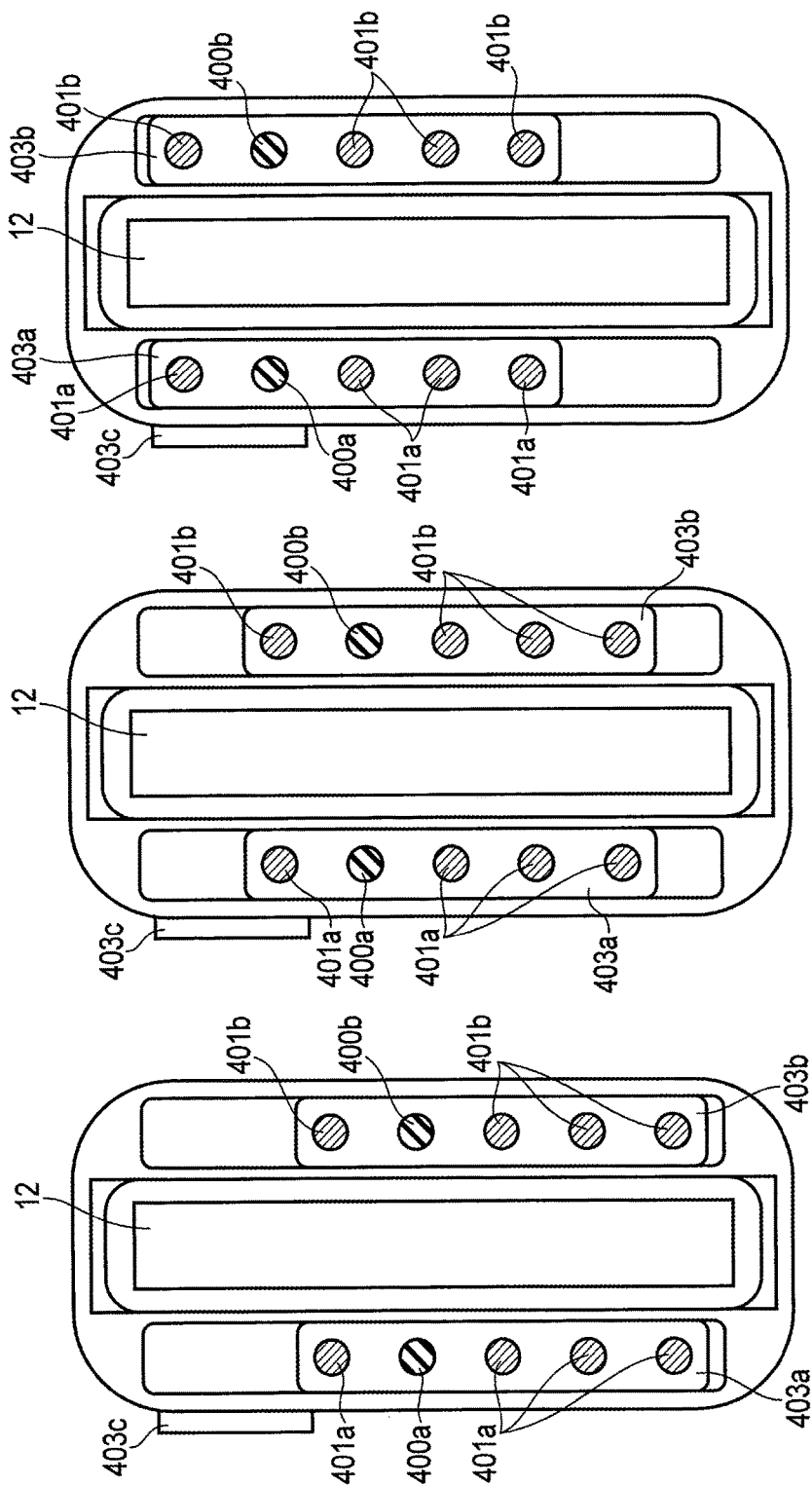
FIGS. 10A, 10B, and 10C are views for explaining sliding operations by a slide mechanism 403a of the probe P exemplarily shown in FIGS. 8 and 9.

FIGS. 10A, 10B, and 10C are views for explaining a sliding operation by the slide mechanism 403a of the probe P exemplified in FIGS. 8 and 9. As in the case shown in FIGS. 3 and 4, it is also possible to use a mechanism which detects an arbitrary slide position by using a potentiometer or the like. However, this makes it easier to perform data analysis by improving the position accuracy of multiple measurements and always maintaining a constant displacement. For this reason, the slide mechanism 403a preferably includes a mechanism capable of temporarily fixing a measurement position, and the slide detector 403c preferably includes a detector which detects the temporarily fixed position.

Note that in the case shown in FIGS. 8, 9, 10A, 10B, and 10C, the optical system slides in a direction toward the side on which the number of optical detection units 401 is smaller. However, this is not exhaustive, and the optical system may be moved to the side on which the number of optical detection units 401 is larger.

(Second Modification)

FIG. 11 shows the second modification of the optical measurement system of the biometrical measurement apparatus 4. This optical measurement system differs from that shown in FIG. 6 in the following points. The system is configured to guide light beams from three light sources 420a1, 420a2, and 420a3 with wavelengths $\lambda 1$, $\lambda 2$, and $\lambda 3$ to the first light emission unit 400a ($\lambda 1$=765 nm, $\lambda 2$=809 nm, and $\lambda 3$=855 nm in the case shown in FIG. 11) and to guide light beams from three light sources 420b1, 420b2, and 420b3 with wavelengths $\lambda 1$, $\lambda 2$, and $\lambda 3$ to the second light emission unit 400b ($\lambda 1$=765 nm, $\lambda 2$=809 nm, and $\lambda 3$=855 nm in the case shown in FIG. 11). The light source 402a1 is driven at a frequency f1. The light sources 420a2 and 420a3 are driven at a frequency f3. The light source 420b1 is driven at a frequency f2. The light sources 420b2 and 420b3 are driven at a frequency f4. Like the arrangement shown in FIG. 4, the multi-channel lock-in amplifier supplies driving signals to the respective light sources. However, this multi-channel lock-in amplifier has four frequencies, and has an arrangement of 8 channels×4, which is four times larger than that shown in FIG. 6. This arrangement includes an analog divider which narrows down 32 ch signals into 16 ch signals.

(Third Modification)

FIG. 12 shows the third modification of the optical measurement system of the biometrical measurement apparatus 4. This optical measurement system differs from that shown in FIG. 11 in the following points. An 8 ch low pass filter is provided on the front stage of a multi-channel lock-in amplifier with an arrangement of 8 channels×4 frequencies. An analog divider is separated from the system. Instead of using the divider, 32 ch signals are converted into digital signals by an ADC, and the signals are standardized by calculation processing. Scanning support information such as approach information is output as speech, and an output unit is provided, which simultaneously displays two types of information, i.e., ultrasonic images and optical measurement results.

(Fourth Modification)

The probe P described above has exemplified the arrangement configured to make the light emission units 400 and the optical detection units 401 slide together. However, this is not exhaustive. For example, one of the light emission unit 400 and the optical detection unit 401 may be fixed, and the other may be made to slide. That is, in principle, it is possible to increase the amount of measurement data if measurement data can be obtained for each of different positional relationships by changing the positional relationship (or the geometric relationship) between an abnormal region (or ultrasonic transmission/reception surface), the light emission unit 400, and the optical detection unit 401.

However, this arrangement becomes a cause of an increase in measurement error in a detected light intensity as compared with the arrangement configured to make the light emission unit 400 and the optical detection unit 401 slide together. Therefore this requires caution.

Figures 13A, 13B:
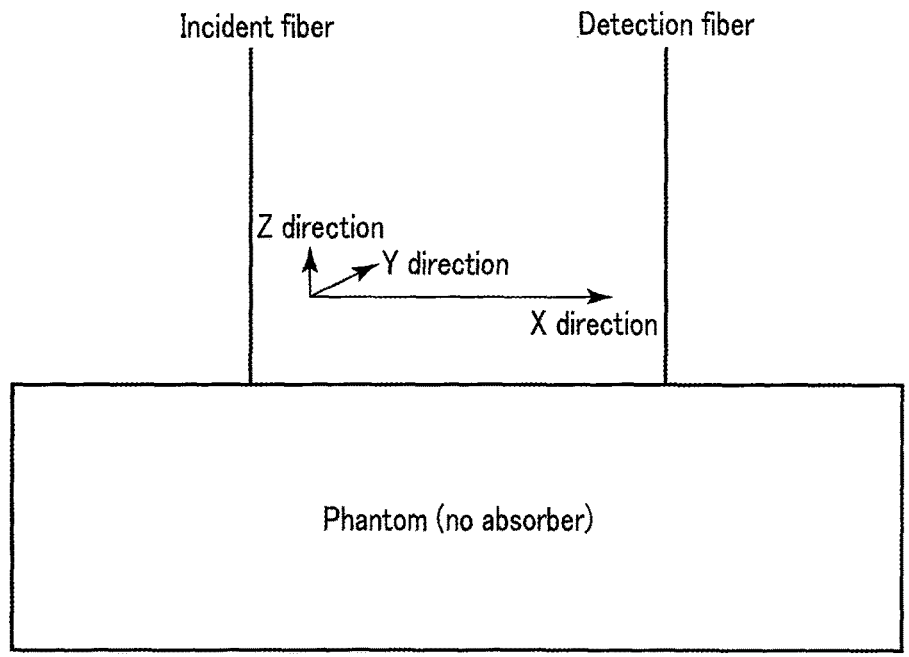
FIGS. 13A and 13B are views showing an example of the position accuracy of the probe and a light intensity error measuring method.
Figure 14B:
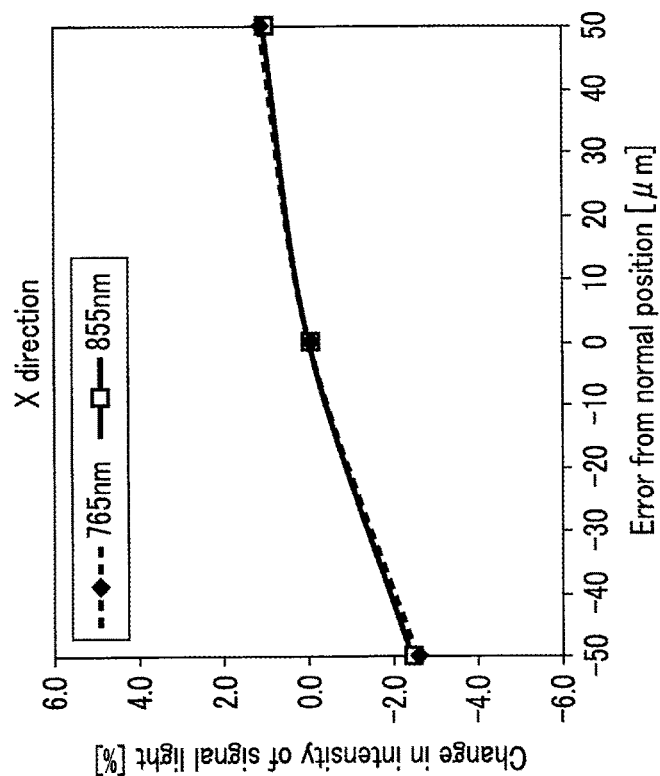
FIGS. 14A and 14B are views showing an example of the position accuracy of the probe and a light intensity error measuring method.
Figure 14A:
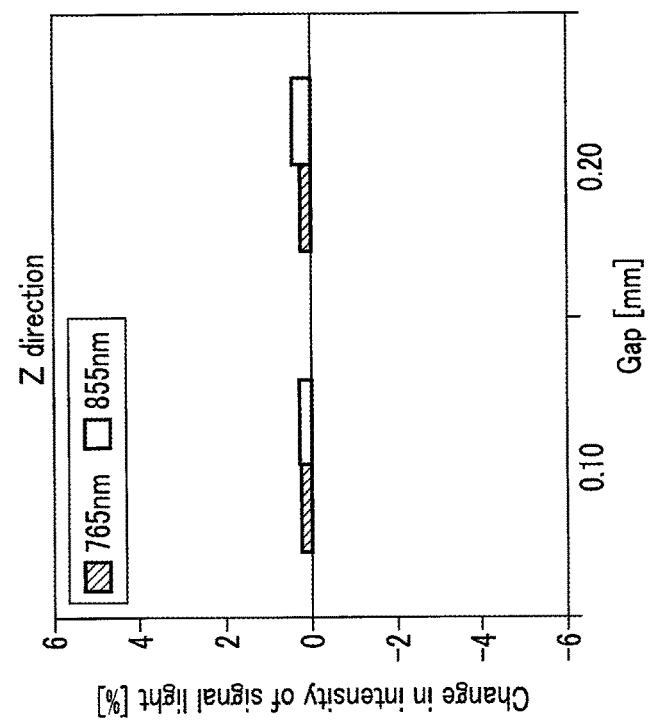

FIGS. 13A and 13B show an example of the position accuracy of the probe and a light intensity error measuring method. Variations in detected light intensity were evaluated as errors under the following conditions: deviations in detected distance (X direction): −50 μm, 0 μm, and +50 μm; deviations in the Y direction: 0 μm, +50 μm, and +100 μm; deviations in contact state (Z direction): 0 μm, +100 μm, and +200 μm; deviations in angle/incident angle (in X-Z plane): −2°, 0°, and 2°; and deviations in detected angle (in X-Z plane): −2°, 0°, and 2°.

FIGS. 14A and 14B and FIGS. 15A and 15B show excerpts from the test results in FIGS. 13A and 13B. It is obvious that deviations in distance and angle cause large variations in measurement data, whereas deviations in contact state cause relatively small variations. It indicates that when making the optical system slide, error factors for incident/detected distances should be avoided, and the emission units and the detection units are more preferably integrated.

FIGS. 16 and 17 show an example of the probe P including the slide mechanism 403a which makes only the optical detection units 401 slide while a light emission unit 400d is fixed. As compared with the case shown in FIGS. 3 and 4, only the optical detection units 401 are integrated and configured to slide in the long side direction of the ultrasonic transmission/reception surface of the ultrasonic probe 12. In contrast to this, the light emission unit 400d is fixed near a short side of the ultrasonic transmission/reception surface. This arrangement is characterized in that measurement errors increase as described above, but the width of an analysis space used for light intensity analysis can be reduced. In addition, by incorporating an analog amplifier whose gain can be automatically adjusted in accordance with a sliding distance, the arrangement has the merit of being capable of broadening the dynamic range of a series of measurements.

The above arrangement of the ultrasonic diagnostic apparatus or biometrical measurement apparatus can achieve the following effects. That is, this arrangement is configured to execute optical biometrical measurement at a plurality of measurement positions while causing the slide mechanism to move at least the plurality of light emission units or the plurality of light detection units along the longitudinal direction of the ultrasonic transmission/reception surface. Therefore, optical signals are acquired at a plurality of measurement positions along the longitudinal direction of the ultrasonic transmission/reception surface. This can increase the amount of data to be used for the calculation of, for example, the depth of an abnormal region from the surface of an object by an amount corresponding to the number of measurement positions. It is therefore possible to guarantee the analysis accuracy of measurement information as compared with the related art.

In addition, the plurality of light emission units and the plurality of optical detection units are moved by the slide mechanism instead of manually. This makes it possible to accurately detect a moving distance and a measurement position while suppressing pressure on the skin at the time of measurement. As a result, it is possible to simply and accurately implement a plurality of optical measurements at different positions for the determination of the position of a diagnostic target region.

The above described "circuitry" means, for example, a central processing unit (CPU), a graphics processing unit (GPU), an application specific integrated circuit (ASIC), a programmable logical device (e.g., a simple programmable logic device (SPLD), a complex programmable logic device (CPLD), and a field programmable gate array (FPGA)), or the like.

Some embodiments of the present invention have been described above. However, these novel embodiments are presented merely as examples and are not intended to restrict the scope of the invention. These embodiments can be carried out in various other forms, and various omissions, replacements, and alterations can be made without departing from the spirit of the invention.

The embodiments and their modifications are also incorporated in the scope and the spirit of the invention as well as in the invention described in the claims and their equivalents.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An ultrasonic diagnostic apparatus comprising:
an ultrasonic probe to transmit an ultrasonic wave from an ultrasonic transmission or reception surface to an object and receive an ultrasonic wave reflected by an inside of the object via the ultrasonic transmission or reception surface;
image generation circuitry to generate an ultrasonic image by using the ultrasonic wave received by the ultrasonic probe;
at least one light emission circuitry to apply light in an absorption wavelength band of a biological component from a surrounding of the ultrasonic transmission or reception surface onto the inside of the object;
a plurality of optical detection circuits arranged around the at least one light emission circuitry and to detect an intensity of light having a specific wavelength which is applied from the at least one light emission circuitry and diffused or reflected by the inside of the object;
a pair of bars arranged on respective sides of the ultrasonic transmission or reception surface and configured to move the at least one light emission circuitry and the plurality of optical detection circuits along a longitudinal direction of the ultrasonic transmission or reception surface to change positional relationships between the ultrasonic transmission or reception surface, the at least one light emission circuitry, and the plurality of optical detection circuits;
analysis circuitry to analyze a change in the light intensity detected for each of different positional relationships between the ultrasonic transmission or reception surface, the at least one light emission circuitry, and the plurality of optical detection circuits; and
scanning support information creation circuitry to generate scanning support information for guiding the ultrasonic probe with respect to the object based on the analyzed change in the light intensity detected for each of different positional relationships, and to output the scanning support information.

2. The apparatus of claim 1, wherein the at least light emission circuitry and the plurality of optical detection circuits are arranged symmetrically with respect to an axis of the ultrasonic transmission or reception surface in the longitudinal direction.

3. The apparatus of claim 1, further comprising an optical filter covering the at least one light emission circuitry and the plurality of optical detection circuits and to transmit light of a plurality of peak wavelength components,
   wherein the pair of bars move the plurality of light emission circuits and the plurality of optical detection circuits via the optical filter.

4. The apparatus of claim 1, further comprising detection circuitry to detect distances to at least either the plurality of light emission circuits or the plurality of optical detection circuits which are moved by the pair of bars.

5. The apparatus of claim 1, further comprising control circuitry to drive the at least one light emission circuitry at different frequencies.

6. A biometrical examination apparatus for use with an ultrasonic probe, the biometrical examination apparatus comprising:
   at least one light emission circuitry to apply light in an absorption wavelength band of a biological component onto an inside of an object;
   a plurality of optical detection circuits arranged around the plurality of light emission circuitry and to detect an intensity of light having a specific wavelength which is applied from the plurality of light emission circuitry and diffused or reflected by the inside of the object;
   a pair of bars adapted to be arranged on respective sides of an ultrasonic transmission or reception surface of the ultrasonic probe and configured to move the at least one light emission circuitry and the plurality of optical detection circuits along a longitudinal direction of the ultrasonic transmission or reception surface to change positional relationships between the ultrasonic transmission or reception surface, the at least one light emission circuitry, and the plurality of optical detection circuits;
   analysis circuitry to analyze a change in the light intensity detected for each of different positional relationships between the ultrasonic transmission or reception surface, the at least one light emission circuitry, and the plurality of optical detection circuits; and
   scanning support information creation circuitry to generate scanning support information for guiding the ultrasonic probe with respect to the object based on the analyzed change in the light intensity detected for each of different positional relationships, and to output the scanning support information.

7. The apparatus of claim 1, wherein the scanning support information corresponds to a degree of adhesion between the ultrasonic probe and a surface of the object.

8. The apparatus of claim 1, wherein the scanning support information corresponds to a proximity of an abnormal region in the object.

9. The biometrical examination apparatus of claim 6, wherein the scanning support information corresponds to a degree of adhesion between the ultrasonic probe and a surface of the object.

10. The biometrical examination apparatus of claim 6, wherein the scanning support information corresponds to a proximity of an abnormal region in the object.

* * * * *